United States Patent
Ackerman et al.

(10) Patent No.: US 6,511,469 B2
(45) Date of Patent: Jan. 28, 2003

(54) CERVICAL OCCLUDING DOUBLE BALLOON CATHETER

(75) Inventors: Bernard Ackerman, Metuchen, NJ (US); Robert M. Landis, Mountainside, NJ (US)

(73) Assignee: Ackrad Laboratories, Inc., Cranford, NJ (US)

( * ) Notice: Subject to any disclaimer, the term of this patent is extended or adjusted under 35 U.S.C. 154(b) by 52 days.

(21) Appl. No.: 09/782,859

(22) Filed: Feb. 14, 2001

(65) Prior Publication Data

US 2002/0111602 A1 Aug. 15, 2002

(51) Int. Cl.[7] .............................................. A61M 31/00
(52) U.S. Cl. .................. 604/515; 604/103.07; 604/523; 604/920; 604/97.01
(58) Field of Search ................................. 604/515, 517, 604/96.01, 103.07, 104, 107, 108, 109, 164.04, 264, 271, 523, 533, 912, 915, 920, 97.01; 606/191–194

(56) References Cited

U.S. PATENT DOCUMENTS

| | | | | |
|---|---|---|---|---|
| 2,610,626 A | * | 9/1952 | Edwards | 427/346 |
| 4,976,692 A | * | 12/1990 | Atad | 604/101.03 |
| 5,147,335 A | * | 9/1992 | Wright | 600/576 |
| 5,312,360 A | * | 5/1994 | Behl | 604/106 |
| 5,352,199 A | * | 10/1994 | Tower | 604/103.07 |
| 5,401,241 A | * | 3/1995 | Delany | 604/103.07 |
| 5,540,658 A | * | 7/1996 | Evans et al. | 604/101.04 |
| 5,624,399 A | * | 4/1997 | Ackerman | 4/103.03 |
| 5,749,883 A | * | 5/1998 | Halpern | 600/114 |
| 5,947,991 A | * | 9/1999 | Cowan | 604/103.07 |

* cited by examiner

Primary Examiner—Lesley D. Morris
Assistant Examiner—Patrick Buechner
(74) Attorney, Agent, or Firm—Duane Morris LLP

(57) ABSTRACT

A catheter device for non-surgical entry into a uterus, includes a tubular body having a lumen extending from a first end thereof to a second end thereof, the lumen having an external opening adjacent to or at the first end for dispensing a diagnostic fluid into the uterus. An elongated balloon is disposed distally on the tubular body for insertion into the cervical canal of the uterus, the balloon having opposing portions which occlude opposing openings of the canal.

20 Claims, 2 Drawing Sheets

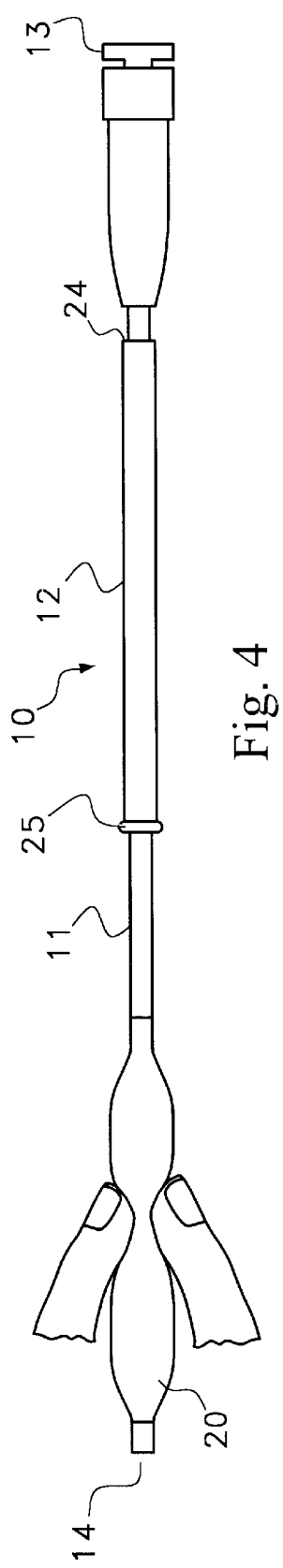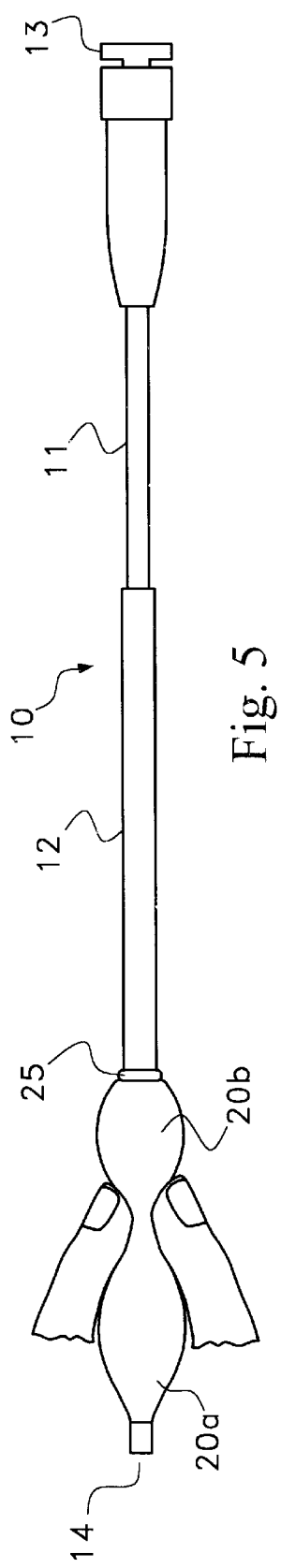

CERVICAL OCCLUDING DOUBLE BALLOON CATHETER

FIELD OF THE INVENTION

The present invention relates to catheters, and in particular, to a diagnostic catheter device with an elongated balloon element disposed adjacent to a distal end thereof, which expands to occlude opposing openings of the cervical canal.

BACKGROUND OF THE INVENTION

Diagnostic procedures which require a non-surgical entry into the uterus are well known. One such procedure known as hysterosalpingography, is a radiographic method for imaging the anatomical structures of the uterus and fallopian tubes. Hysterosalpingography involves inserting a fine flexible catheter through the cervical canal and injecting a contrast medium, such as an iodinated fluid, into the uterus. Radiography is then carried out to provide imaging information pertaining to the subject uterus and fallopian tubes.

Another well known diagnostic procedure which entails the non-surgical entry into the uterus is called hysterosonography. This procedure also employs a fine flexible catheter that is inserted into the cervical canal of the uterus. The catheter in this procedure enables the physician or technician to inject a sterile saline or water solution into the uterus to expand it so that an ultrasound scanner can be used to sonographically observe the uterus.

The catheters typically used in both procedures have some type of means for sealing off the uterus after injection of the fluid to prevent back-flow into the vaginal canal. One commonly employed means is an inflatable intrauterine balloon made from an elastomeric material. The balloon is usually disposed adjacent the distal tip of the catheter. A first lumen provided in the catheter communicates with the interior of the balloon to enable inflation and deflation of the balloon with an inflation syringe. A second lumen provided in the catheter enables a desired diagnostic fluid to be injected into the uterus with an injection syringe.

Such catheters are operated by inserting the distal tip thereof through the cervical canal and into the uterus with the intrauterine balloon deflated. The insertion of the distal tip operates to position the deflated intrauterine balloon in the uterus or cervical canal. Once positioned, the inflation syringe is used to inflate the intrauterine balloon with air or a saline solution to seal and block the cervical canal. The injection syringe can then be used to inject the desired diagnostic fluid into the uterus.

One problem associated with these balloon catheter designs is that they are relatively expensive to manufacture. Therefore, a less expensive diagnostic balloon catheter device is needed.

SUMMARY OF THE INVENTION

A catheter device for non-surgical entry into a uterus, comprises a tubular body having a lumen extending from a first end thereof to a second end thereof, the lumen having an external opening for dispensing a diagnostic fluid into the uterus. An elongated balloon is disposed distally on the tubular body for insertion into the cervical canal of the uterus, the balloon having opposing portions which occlude opposite openings of the cervical canal.

Another aspect of the invention involves a method for non-surgically entering a uterus to dispense a diagnostic fluid therein, the method comprises providing a catheter device comprising a tubular body having a lumen extending from a first end thereof to a second end thereof, an elongated balloon disposed distally on the tubular body, and an inflation sleeve slidably disposed over the tubular body. The first end of the tubular body is inserted through the cervical canal of the uterus so that the elongated balloon is positioned within the canal with opposing portions of the balloon adjacent openings of the canal. The inflation sleeve is slid over a section of one of the opposing portions of the balloon thereby inflating the opposing portions of the balloon to occlude the openings of the canal. The diagnostic fluid is then dispensed through the lumen of the tubular body into the uterus.

BRIEF DESCRIPTION OF THE DRAWINGS

The advantages, nature, and various additional features of the invention will appear more fully upon consideration of the illustrative embodiments now to be described in detail in connection with accompanying drawings wherein:

FIG. 4 is a diagrammatic view of the catheter device of the invention inserted into the cervical canal of a subject uterus prior to inflation of the balloon portions; and FIG. 5 is a diagrammatic view of the catheter device of the invention inserted into the cervical canal of a subject uterus after inflation of the balloon portions.

It should be understood that the drawings are for purposes of illustrating the concepts of the invention and are not necessarily to scale.

DETAILED DESCRIPTION OF THE INVENTION

Figure 1:
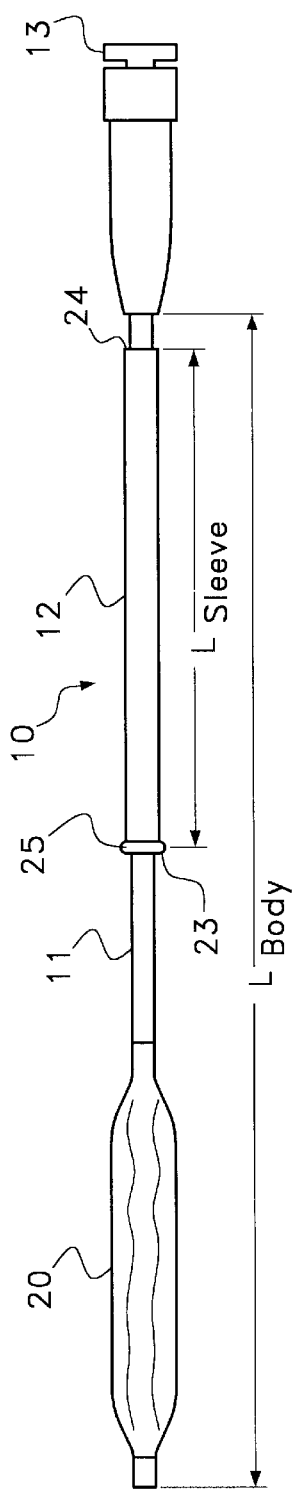
FIG. 1 is an elevational view of a catheter device according to an exemplary embodiment of the invention.

Referring to the drawings wherein like reference numerals identify similar or like elements throughout the several views and initially to FIG. 1, there is shown a diagnostic catheter device 10 according to an exemplary embodiment of the invention. The catheter device 10 generally comprises a flexible tubular body 11, a semi-rigid inflation sleeve 12, and optionally, a stylet assembly 13.

Figure 2:
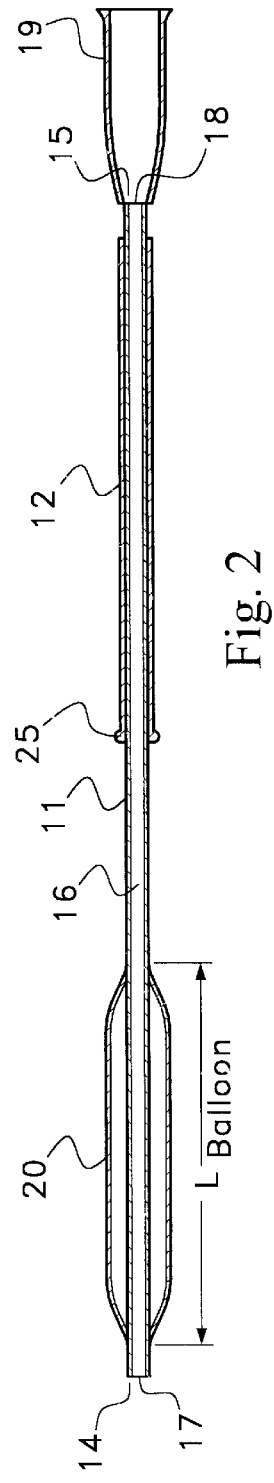
FIG. 2 is a sectional view of the catheter of the device.

As shown in FIG. 2, the tubular body 11 of the catheter device 10 defines a distal end 14 and a proximal end 15. The body 11 includes a lumen 16 that extends the entire length $L_{body}$ thereof and communicates with the external environment via distal opening 17 and proximal opening 18 at the distal and proximal ends 14, 15 of the body 11. The lumen 16 provides a fluid communication path for injecting a diagnostic fluid, such as saline or a contrast medium, into the uterine cavity. The lumen 16 also provides a means for inserting diagnostic instruments into the uterine cavity. A conventional female Luer hub connector 19 is provided at the proximal end 15 of the catheter body 11 for connecting a male Luer tip connector. Non-Luer hub connectors may also be used depending on the instrument to be attached. The catheter body 11 may be made from an opaque or clear flexible material such as polyurethane or any other suitable material.

Referring to FIGS. 1 and 2, an elongated inflatable balloon 20 (shown in the deflated state), about 4 inches in length $L_{balloon}$, is sealingly affixed to and encloses a distal portion of the catheter body 11. The balloon 20 may be made from an elastomeric material such as polyurethane, poly(vinyl chloride) or any other suitable material. Although partially deflated, the balloon 20 contains a small residual volume of air and/or saline solution. The elongated construction of the balloon 20 enables it to be positioned in the cervical canal such that distal and proximal end portions 20a, 20b of the balloon 20 extend past the openings of the canal (FIG. 5). The distal and proximal portions 20a, 20b of the balloon 20 are inflated and deflated by the operation of the inflation sleeve 12 as will described further on.

Figure 3:
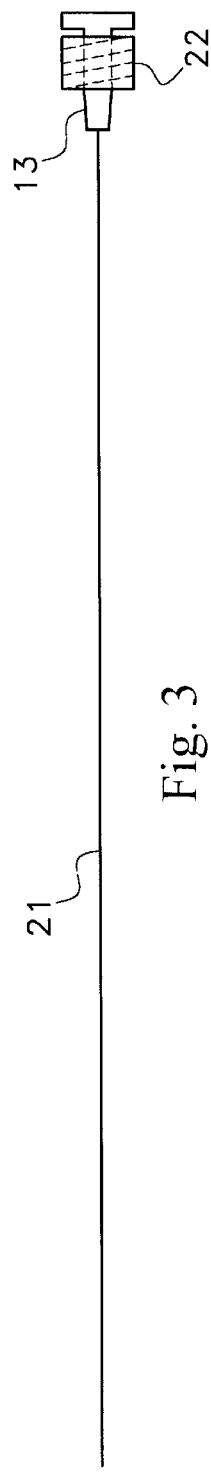
FIG. 3 is an elevational view of the stylet assembly of the catheter device.

As shown in FIG. 3, the optional stylet assembly 13 of the catheter 10 comprises a wire 21 (stylet) that extends through the lumen 16 of the catheter body 11 from the proximal end 15 thereof to a point approximately adjacent a point 1 to 2 cm from the distal end of the balloon 20. The proximal end of the wire 21 is permanently affixed to a central portion of a male Luer tip connector 22. The stylet 21 is threaded into the lumen 16 of the catheter body 11 and retained therein by coupling the catheter body and stylet assembly connectors 19, 22 together. The stylet assembly 13 is typically employed to prevent the catheter 10 from bending and flexing excessively in the vagina, in cases where insertion of the catheter 10 into the cervical canal is difficult. The stylet 21 can then be removed so that a syringe (not shown) containing a diagnostic fluid can be connected to the connector 19 of the catheter body 11 and operated to inject the diagnostic fluid into the uterine cavity through the lumen 16 of the catheter body 11.

Referring again to FIG. 1, the inflation sleeve 12 of the catheter device 10 has a distal end 23 and a proximal end 24. The inflation sleeve 12 may be made from any suitable semi-rigid material such as polypropylene. The distal end 23 of the sleeve 12 terminates with an outwardly extending rim 25. The inflation sleeve 12 has a length $L_{sleeve}$ which may be about 40% percent of the length $L_{body}$ of the catheter body 11. This enables the inflation sleeve 12 to be slidably moved along the catheter body 11 in both the distal and proximal directions to inflate and deflate the elongated balloon 20.

Referring to FIG. 4, the catheter device 10 may be operated by positioning the inflation sleeve 12 proximally on the catheter body 11, introducing the catheter device 10 into the vaginal canal and inserting the distal end 14 of the catheter body 11 through the cervical canal so that the distal and proximal portions 20a, 20b of the balloon are positioned adjacent the exterior and interior OS of the cervical canal. If necessary or desired, the stylet assembly 13 can be used to stiffen the catheter body 11 to aid in the insertion of the catheter body 11 into the cervical canal. The stylet assembly 13 may be assembled to the catheter body 11 by inserting the distal end of the stylet 21 into the catheter connector 19 and threading the stylet 21 through the lumen 16 of the catheter body 11 via the opening 18 at the proximal end 15 thereof and fastening the connectors 19, 22 of the body 11 and stylet assembly 13.

As shown in FIG. 5, the distal and proximal portions 20a, 20b of the balloon 20 are inflated by sliding the inflation sleeve 12 distally along the catheter body 11 so that the sleeve 12 slides over the end of the proximal portion 20b of the balloon 20. As the sleeve slides over the proximal portion 20b of the balloon 20, the volume of air or saline contained therein is redistributed and inflates and expands the distal and proximal portions 20a, 20b of the balloon 20, thereby forming a double balloon structure which conforms to and thus occludes the exterior and interior OS of the cervical canal and sealingly affixes the catheter device 10 in place therein.

The stylet assembly 13 can now be removed from the catheter body 11 and a syringe filled with a diagnostic fluid such as saline or a contrast dye, can now be operated to inject the diagnostic fluid into the uterine cavity of the uterus for imaging.

When it is desirable to deflate the portions of the balloon 20, the inflation sleeve 12 is moved proximally along the catheter body 11. This allows the air and/or saline in the distal and proximal balloon portions 20a, 20b to be redistributed throughout the interior of the balloon 20 so that the catheter device 10 can be withdrawn through the cervix.

Although the catheter device 10 has been described for non-surgical entry into the uterine cavity, one of ordinary skill in the art will recognize its usefulness in other related procedures.

Further, while the foregoing invention has been described with reference to the above embodiments, various modifications and changes can be made without departing from the spirit of the invention. Accordingly, all such modifications and changes are considered to be within the scope of the appended claims.

What is claimed is:

1. A catheter device comprising:
   a tubular body having a lumen extending from a first end thereof to a second end thereof, the lumen having an external opening for dispensing a diagnostic fluid;
   an elongated balloon disposed distally on the tubular body for insertion into a canal of a body, the balloon having opposing portions which occlude openings of the canal when inflated; and
   an inflation sleeve slidably disposed over the tubular body, the sleeve being moveable over the elongated balloon to inflate the opposing portions of the balloon.

2. The catheter device according to claim 1, wherein the tubular body is flexible.

3. The catheter device according to claim 1, wherein the inflation sleeve is semi-rigid.

4. The catheter device according to claim 1, wherein the portions of the balloon define a double balloon structure when the balloon is inserted in the canal.

5. The catheter device according to claim 1, wherein the balloon is made from an elastomeric material.

6. The catheter device according to claim 1, wherein the tubular body is made from a polyurethane material.

7. The catheter device according to claim 1, further comprising a stylet removeably inserted into the lumen of the tubular body through the second end thereof.

8. The catheter device according to claim 1, wherein the external opening of the tubular body is adjacent the first end thereof.

9. The catheter device according to claim 1, wherein the external opening of the tubular body is at the first end thereof.

10. A catheter device for non-surgical entry into a uterus to dispense a diagnostic fluid therein, the catheter comprising:
    a tubular body having a lumen extending from a first end thereof to a second end thereof, the lumen having an external opening for dispensing the diagnostic fluid into the uterus;
    an elongated balloon disposed distally on the tubular body for insertion into the cervical canal of the uterus, the balloon having opposing portions which occlude openings of the canal; and
    an inflation sleeve slidably disposed over the tubular body, the sleeve being moveable over the elongated balloon to inflate the opposite portions of the balloon.

11. The catheter device according to claim 10, wherein the body is flexible.

12. The catheter device according to claim 10, wherein the inflation sleeve is semi-rigid.

13. The catheter device according to claim 10, wherein the portions of the balloon define a double balloon structure when the balloon is inserted in the cervical canal.

14. The catheter device according to claim 10, wherein the balloon is made from an elastomeric material.

15. The catheter device according to claim 10, wherein the tubular body is made from a polyurethane material.

16. The catheter device according to claim 10, further comprising a stylet removeably inserted into the lumen of the tubular body through the second end thereof.

17. A method for non-surgically entering a uterus to dispense a diagnostic fluid therein, the method comprising the steps of:
   providing a catheter comprising a tubular body having a lumen extending from a first end thereof to a second end thereof, an elongated balloon disposed distally on the tubular body, and an inflation sleeve slidably disposed over the tubular body;
   inserting the first end of the tubular body through the cervical canal of the uterus so that the elongated balloon is position within the canal with opposing portions of the balloon adjacent openings of the canal;
   sliding the inflation sleeve over a section of one of the opposing portions of the balloon thereby inflating the opposing portions of the balloon to occlude the openings of the canal; and
   dispensing the diagnostic fluid through the lumen of the catheter into the uterus.

18. The method according to claim 17, wherein the catheter further comprises a stylet removeably inserted into the lumen of the tubular body through the second end thereof and further comprising the step of removing the stylet from the tubular body of the catheter prior to the dispensing step.

19. The method according to claim 17, further comprising the step of proximally sliding the inflation sleeve off the section of the balloon portion to deflate the opposing balloon portions.

20. The method according to claim 19, further comprising the step of withdrawing the first end of the tubular body through the cervical canal of the uterus.

* * * * *